(12) United States Patent
Feliciano

(10) Patent No.: US 6,770,057 B2
(45) Date of Patent: Aug. 3, 2004

(54) QUICK FLOW CONTROL FOR FLEXIBLE TUBING

(75) Inventor: Ari J. Feliciano, Mayaguez, PR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 142 days.

(21) Appl. No.: 10/286,540

(22) Filed: Oct. 31, 2002

(65) Prior Publication Data

US 2004/0087911 A1 May 6, 2004

(51) Int. Cl.[7] ............................................. A61M 5/00
(52) U.S. Cl. ................................................ 604/250; 251/7
(58) Field of Search ...................... 251/4, 7; 137/269, 137/271; 604/80, 93.01, 246, 247, 248, 250, 251, 256, 259; 222/206–207, 209, 211–213, 476–477, 544, 545

(56) References Cited

U.S. PATENT DOCUMENTS

| | | | | |
|---|---|---|---|---|
| 2,954,028 A | * | 9/1960 | Smith | 604/80 |
| 3,411,534 A | * | 11/1968 | Rose | 137/595 |
| 3,915,167 A | * | 10/1975 | Waterman | 604/250 |
| 4,072,292 A | | 2/1978 | Banon | 251/331 |
| 4,121,584 A | | 10/1978 | Turner et al. | 128/214 E |
| 4,142,523 A | | 3/1979 | Stegeman | 128/214 R |
| 4,180,067 A | | 12/1979 | Derlien | 128/214 F |
| 4,262,668 A | | 4/1981 | Schmidt | 128/214 R |
| 4,280,680 A | | 7/1981 | Payne | 251/175 |
| 4,343,305 A | | 8/1982 | Bron | 128/214 R |
| 4,375,882 A | | 3/1983 | Schreiber, Jr. | 251/266 |
| 4,382,453 A | * | 5/1983 | Bujan et al. | 138/40 |
| 4,432,468 A | | 2/1984 | Stiff et al. | 222/55 |
| 4,493,709 A | * | 1/1985 | Smith | 604/246 |
| 4,552,336 A | | 11/1985 | Pastrone | 251/331 |
| 4,616,802 A | * | 10/1986 | Tseng et al. | 251/7 |
| 4,950,255 A | * | 8/1990 | Brown et al. | 604/250 |
| 4,979,644 A | | 12/1990 | Meyer et al. | 222/94 |
| 5,318,515 A | * | 6/1994 | Wilk | 604/30 |
| 5,423,769 A | * | 6/1995 | Jonkman et al. | 604/250 |
| 5,520,661 A | | 5/1996 | Lal et al. | 604/246 |
| 5,925,023 A | * | 7/1999 | Hiejima | 604/246 |
| 6,213,986 B1 | | 4/2001 | Darling, Jr. | 604/248 |
| 6,280,408 B1 | | 8/2001 | Sipin | 604/65 |

* cited by examiner

*Primary Examiner*—Loan H. Thanh

(57) ABSTRACT

A flow control system includes a control device for intravenous (IV) tubing or other flexible or compressible tubing, wherein selectors are depressed to cause different amounts of compression of the tubing to partially flatten or squeeze the tube, and, hence, to cause different flow-rates of liquid through the tubing. The flow control system may have a housing surrounding a portion of the tube and the selectors may be moveable in the housing away from the tube to an outward position and moveable in the housing to an inward position against and pressing on the tube so that the selector compresses the tube into reduced-cross-section shape to reduce flow through the axial fluid passage of the tube. The selectors may be positioned in series along the tube, with each selector contacting a different portion of the tube.

14 Claims, 3 Drawing Sheets

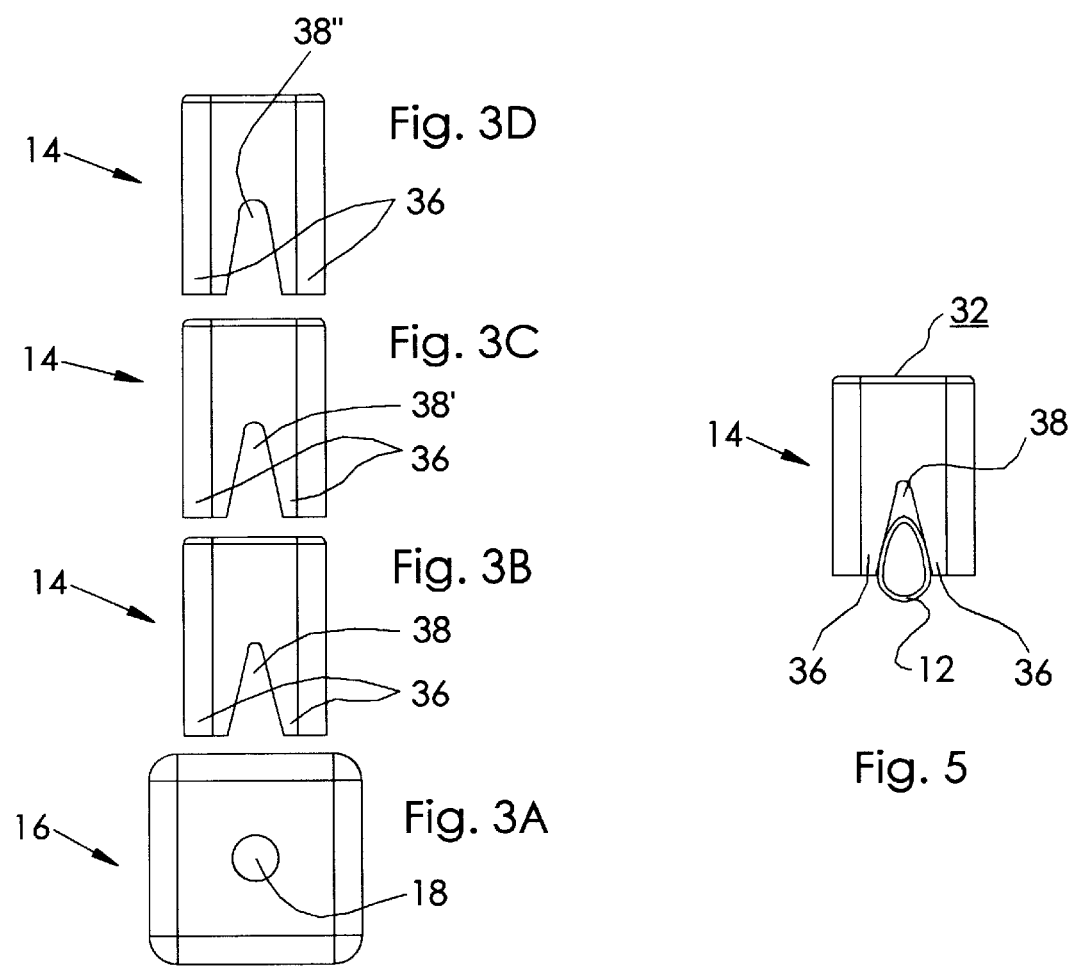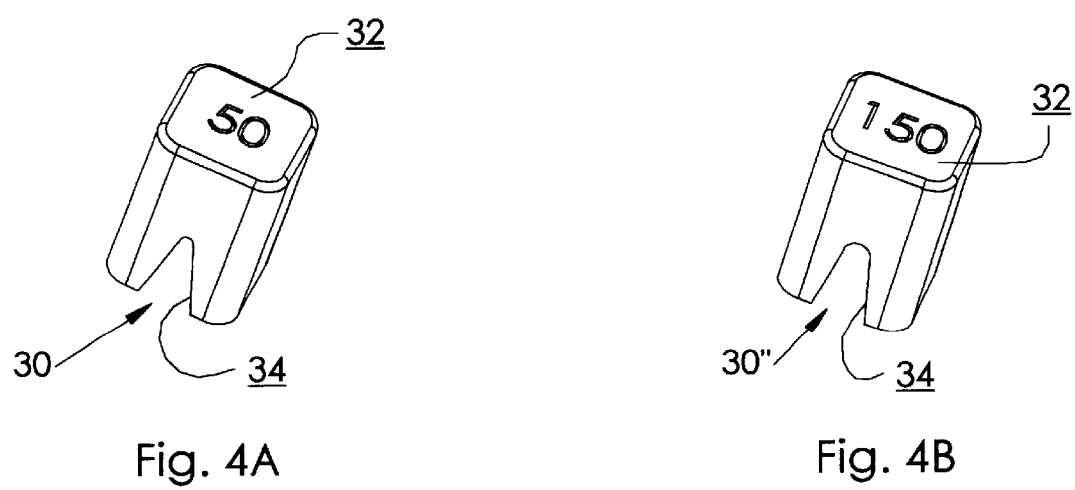

US 6,770,057 B2

QUICK FLOW CONTROL FOR FLEXIBLE TUBING

BACKGROUND OF THE INVENTION

In hospitals, clinics or field medical operations, intravenous (IV) tubes are regularly used in situations that necessitate selection of various specific IV flow-rates. Prior IV control systems tend to be either difficult to monitor and adjust accurately, or too complex, heavy, and expensive for many situations and locations.

Existing in-line pump-driven flow control systems are typically costly, complex, and/or heavy, and reply on a power source other than gravity. In-line pump systems exist that have complex control systems, for example, which compare the actual flow-rate to the desired flow-rate to produce error signals that are then utilized to adjust the actual flow-rate. Such complex devices are impractical for use in remote field situations where low cost and simplicity are important.

Another approach to flow control in an intravenous system is to provide a manifold having multiple connection points for tubing, with each connection point corresponding to a different flow rate. Such a connector may address the need for reduced cost but is complex to use. Further, such a connector may create a contamination risk, by exposing the fluid to the environment when the tube is moved from one manifold connection point to the next.

Flow adjustment in IV tubes has also been attempted by means of providing a folded IV tube and controlling flow by limiting the degree of unfolding of a folded IV tube. Such a system has the benefit of the flow control apparatus not being in-line, but such a system tends to be inaccurate and difficult to control.

SUMMARY OF THE INVENTION

A flow control system comprises a fluid conduit tube having a flexible or compressible wall defining an interior axial fluid passage, and a control device having a plurality of selector units moveable to press on the tube so that the selector units compress the tube to have a reduced-cross-section, thus, reducing flow through the axial fluid passage of the tube. The selector units preferably move inward toward the tube to an inward position that compresses the tube and outward to an outward position that releases the compressive force on the tube. The selector units are adapted so that, in their inward positions, they cause different amounts of flow restriction, thus, corresponding to different flow rate selections.

The flow control device may be adapted for flexible conduits that deliver fluids to various processes, both medical and otherwise. The preferred embodiment of the flow control device is particularly well-adapted for IV tubes, wherein there are typically a small number of standard flow-rates, and wherein it is important to minimize the contact of the fluid with valves or other equipment that might contaminate the fluid with microbes or chemicals. The preferred embodiment of the flow control device comprises a plurality of discrete adjustments, corresponding to the preferred or standard flow-rates for IV treatments.

BRIEF DESCRIPTION OF THE DRAWINGS

FIG. 3A is an end view of the housing of the embodiment of FIGS. 1 and 2.

FIGS. 3B, C and D are side views of the low, medium, and high flow selector buttons, respectively, of the embodiment of FIGS. 1 and 2.

FIG. 4A is a perspective view of the 50 cc/hour selector button of the embodiment of FIGS. 1–3.

FIG. 4B is a perspective view of the 150 cc/hour selector button of the embodiment of FIGS. 1–3.

FIG. 5 is a schematic end view of a selector unit compressing an IV tube.

DETAILED DESCRIPTION OF THE PREFERRED EMBODIMENTS

Figure 1:
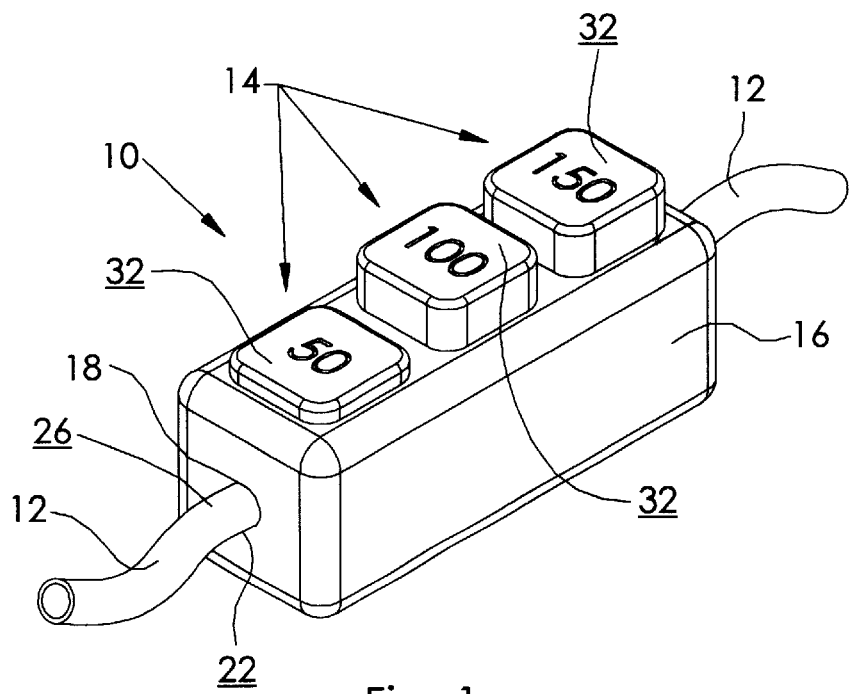
FIG. 1 is a perspective view of the one embodiment of the invented flow control device for flexible tubing.
Figure 2:
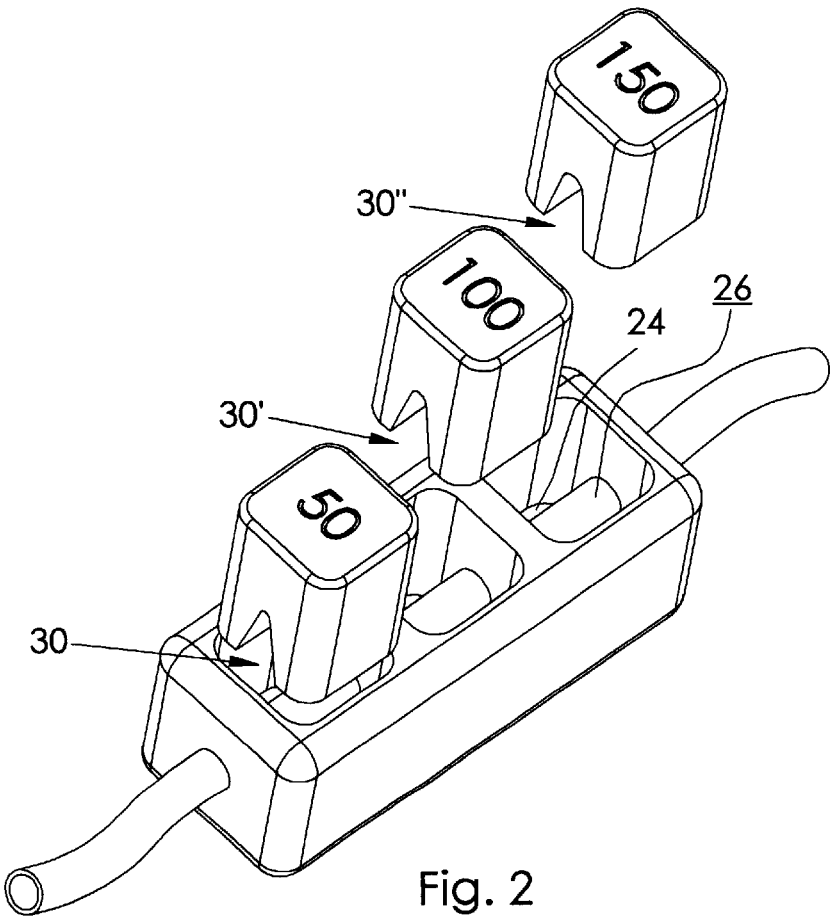
FIG. 2 is an exploded perspective view of the device of FIG. 1, with its three flow-rate selector units removed from the housing.

Referring to the figures, there are shown some, but not the only, embodiments of the flow control device. The preferred embodiment comprises apparatus that variably applies force to the outside surface of a flexible tube to regulate the flow-rate of fluid within the tube. The preferred embodiment is a multiple-push-button-style flow regulator that compresses an intravenous (IV) tube or another tube to restrict the flow-rate, such that each button is indexed to allow a different flow-rate through the tube. The preferred embodiment enables IV flow control without the use of in-line technologies that contact the IV fluid, and especially without complex and heavy IV fluid pumps.

The preferred IV tube flow control device includes a housing to support a plurality of selector units, each for selecting a different flow-rate, aligned in series along the tube. Each selector unit is used for griping onto, or pushing against, the tube's outer surface in varying amounts, so that the selector units preferably comprise compression and/or clamping. The amount of clamping or compression is defined by a predetermined limit that correlates to a specific flow constriction in the IV tube, enabling indexed IV flow regulation.

The multiple selector units in series along the IV tube are preferably independently engageable, so that each enables a distinct flow-rate. These selector units are slidable, pivotal, or otherwise moveable to press against the outer surface of the IV tube to partially collapse the tube. Each selector unit further comprises an interface mechanism for access by the user for actuating the selector unit. The interface mechanism may be a button for being pushed, a lever for being flipped, a threaded member for being turned, or another mechanism that is leveraged or buttressed against the housing to allow force on the clamping/compression system. Preferably, the interface mechanism actuates the clamping/compression system in a single increment, so that each selector unit is moveable to affect only a single flow-rate chance, not a continuum of flow-rates.

Preferably, the selector units are biased into the non-clamping, non-compressing position. The preferred push-button-style selector unit, therefore, is resistively loaded when depressed into the inward, clamping/compressing position. The biasing means may include the resilient IV tube naturally pushing outward on the selector unit, or other spring or resilient means. A latch or lock holds the push-button selector unit in the compression position until released by the user.

The push-buttons may each comprise a bottom surface that presses against the flexible or compressible tubing, and each bottom surface is sized and/or shaped so that the pressing constricts the tubing to result in a commonly-used flow-rate for the particular application. The control device does not contact the inside of the tubing or the liquid and so does not pose a contamination risk.

In the preferred embodiment of the Figures, the flow control device 10 is shown engaging and cooperating with flexible tubing. The flow control device 10 is placed around the IV tube 12 so that the discrete-adjustment systems are disposed in series along a length of the tube. Preferably, the control device 10 is placed on a single, continuous, and uncut length of tubing, wherein neither the interior of the tube nor the fluid contained therein is contacted by any portion of the control device or exposed to the atmosphere. The preferred discrete adjustment systems are compression-causing selector units 14 that are each moveable to a "select position" (tube-compressing position) and a de-select position (less- or preferably no-tube-compressing position). Each selector unit, in its select position, causes a specific, different amount of compression of the IV tube and therefore a different amount of reduction of radial cross-sectional area of the tube and corresponding flow restriction.

The tubing with which the preferred embodiment is used is a hollow, flexible-walled fluid conduit, preferably conventional IV tubing, other polyvinyl chloride (PVC) tubing, or other plastic tubing that can be flattened or partially flattened when pressure is applied to the side(s) of the tubing, for example, either by squeezing two sides of the tubing together or applying force on one side of the tubing to press it against a resistant surface. Preferably, the tubing is of such a composition and wall thickness that it may be repeatedly squeezed/pressed and still spring back to its original shape. The preferred tubing diameters are those of conventional IV tubing of various types, but other tubing and other diameters may be used for other applications of flow control device. The preferred device may be manufactured by one of skill in the art, after viewing this Description and Drawings, to fit with various diameters and flexibilities of tubing.

The housing 16 of the flow control device 10 is placed around the tubing 12, so that the tubing extends, in effect, through a bore 18 in the housing. A bottom side 22 of the tubing is against or near an interior bottom wall 24, which acts as a support surface against which the tubing is compressed. The top side 26 of the tubing is positioned for contact with the clamping/compression systems 30 of the plurality of selector units 14. The housing 16 may split longitudinally into two halves, for example, for being fastened around the tubing in clam-shell or clamp fashion. Or, the device 10 may be adapted to receive the tubing 12 slid longitudinally through the housing bore 18 and adapted to be fastened to the tubing to prevent further sliding of the device 10 relative to the tubing 12.

The selector units 14 each comprise a button top 32, serving as the user interface mechanism, for pushing the button to slide in the housing 16, transversely to the axis of the tubing 12. The bottom of each selector unit is the compression system 30, which preferably comprises tubing contact surface 34 with two arms 36 and longitudinal channel 38, 38', 38" that face the top side 26 of the tubing. When the button selector unit is pushed from the outward, de-select position into the inward, select position, the tubing contact surface 34 moves a predetermined radial distance inward toward the tubing, and, hence, pushes the top side 26 toward the bottom side 22 of the tubing.

Given that all selector units preferably travel a predetermined and equal distance when pressed, the axial movement of the tubing contact surface 34 is equal to that predetermined amount. The effect of this movement on the tubing, therefore, is determined by the shape of the bottom surface (tubing contact surface 34) of the selector unit.

The preferred bottom surface shape is shown to best advantage in FIGS. 3B–D and 4A, and 4B. The two arms 36 protrude downward on two sides of the tubing, receiving the tubing in longitudinal channel 38, 38', 38". As shown in FIG. 5, the channel receives the tubing and compresses the tubing wall, especially from the sides and/or the top and sides. The bigger the channel is and wider the arm spacing is, the less the tubing is compressed. One may see in FIGS. 3B, C and D, a narrow channel 38, moderate channel 38', and a wide channel 38", creating the three set increments of compression and flow restriction.

The inventor envisions shapes for a tubing contact surface other than the arm-and-channel design. For example, a convex shape may be used to press down on the tubing from the top, rather than the convex shape of the arm-and-channel design that presses on the tubing from two sides and, optionally, from the two sides and the top.

The preferred device may be calibrated for the flow-rates of 50 cc/hour, 100 cc/hour, and 150 cc/hour, which are commonly-preferred flow-rates for many medical treatments. This calibration is typically achieved by the selector unit bottom surfaces (contact surfaces 34) being shaped and sized appropriately at manufacture, but other methods are envisioned, for example.

If repeated flow-rate adjustment renders a length of tubing inflexible or unresilient, so that flow adjustment becomes less accurate or impossible, new tubing should be used or the flow control device may be moved a distance along the tubing to a fresh and resilient spot in the tubing. Alternatively, the inexpensive flow control device is used only for a short time and/or for a few flow adjustments before it is discarded, thus, disposing of the tubing and flow control before the tubing and/or controller are fatigued.

The latching/unlatching systems (not shown) are for holding a selector in position once it is pressed. These may be designed by one of skill in the art after this Description and the attached drawings are read and viewed. The latch/locking means may be designed in various ways, for example, so that the latch/locking means is released by simply acting again on the same interface mechanism, for example, pressing the same button again, or, by operating another of the interface mechanisms to select another flow-rate and automatically release the previously selected clamping/compression system. For example, for a push-button selector unit, conventional push-button on-off technology may be applied, in which a first push engages (turns on) the button and a second push disengages (turns off) the button. Alternatively, means may be used such that a first push on one button engages that first selector unit, and the next push, on a second button, engages that second selector unit while simultaneously disengaging (popping up) the first selector unit. Such a system, that ensures that only one button is selected (depressed) at one time, may be important for IV fluids wherein accuracy and consistency of flow-rate are more crucial.

While the three standard flow-rates for many medical treatments are 50 cc/hour, 100 cc/hour, and 150 cc/hour, there may be other flow-rates that are desirable for special circumstances or special medications or IV tubing. For example, various liquids may be used that have different flow characteristics and that flow differently through a given tubing and restriction. Therefore, selector units 14 may be made for alternative flow-rates and liquids. The housing of a single control device 10 may be made to accommodate many various selector units for many different flow-rates and/or different liquids, and the selectors may be installed in the field or medical facility. Preferably, therefore, selector units are removable and replaceable, so that the selector units may be changed and interchanged. The selector units are preferably clearly labeled with the flow-rate, and, if made for a particularly liquid, with the name of the liquid with which it is designed to be used.

Preferably, there is a minimum of structure in the control device, so that it may be made to be light-weight and durably. Preferably, the user's action on the control device directly causes the movement of the compression surface of the selector units, so that there is a sure and certain flow adjustment. Preferably, there are no motorized parts in the control device and no contact between the control device and the inside of the tubing or the tubing contents. Preferably, the control device does not have any continuously-adjustable structure, but only the plurality of separate and independent selectors, wherein each selector only can cause a single and discrete flow-rate adjustment. This way, there is little guesswork or chance for error by the users, as long as he/she is trained on proper installation of the control device on the proper tubing, and is trained to recognize the appearance and "feel" of the control device during selection of a flow-rate.

Figure 6:
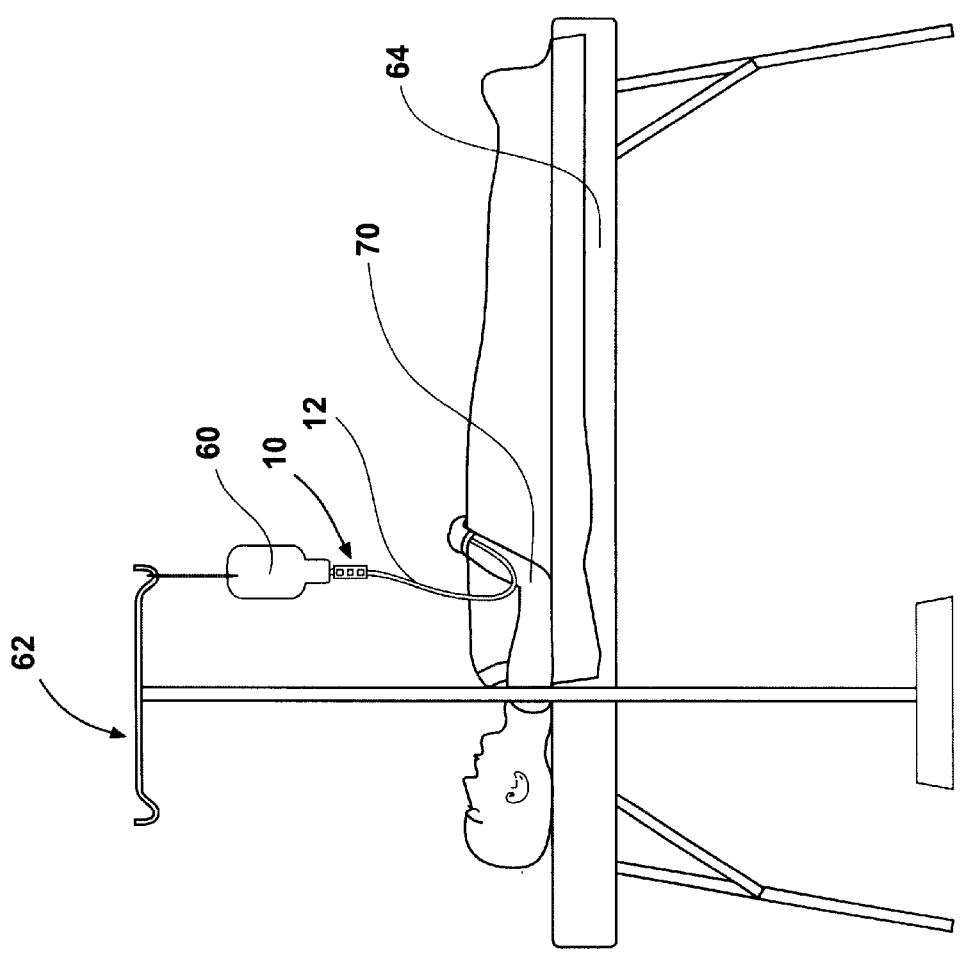
FIG. 6 is a schematic view of the embodiment of FIGS. 1 and 2 connected to an IV tube and IV fluid bag hanging at an elevated position for a gravity-flow operation.

The control device may be made to be light-weight and disposable, so that armed services medics, Emergency Medical Teams, and other field or quick-response medical personnel may conveniently and aseptically set up and adjust an appropriate IV for patients. In applications such as that in FIG. 6, the control device 10 will be installed as one, or the only, control device for an IV tube 12 attached to a gravity-flow IV fluid bag/container 60 hanging at an elevated position on a hanger 62 above a bed 64, operating table, or stretcher. In this way, the preferred control device 10 may be used without a pump or other pressurized source, with the elevated fluid from the bag/container 60 filling the IV tube 12 and providing the force behind the flow of fluid through the control device 10 and into the patient 70. In such embodiments, the control device 10 selector units may be pre-calibrated/pre-modified to produce the desired flow rates for the desired type of fluid 72 and gravity-flow arrangement to be used. For example, the manufacturer may supply a control device with selector units that are properly shaped and sized to produce the proper flow-rates for a particular fluid, or group of fluids similar in viscosity and density, in a hanging-IV-bag set-up.

For other applications, such as those using a pump or other pressure source, the control device may be designed or modified for that particular system. This may be done by testing/calibrating the control device in the particular system, and selecting the size and shape of the selector units from a variety of available selector units, or modifying the size and shape of selector units, to produce the desired flow rates in that system. In this manner, a control device is likely to be matched with and preferably provided with the fluids and/or the equipment for a particular system, for example, for a particular group of fluids and a particular means of providing pressure for fluid flow.

The preferred method, therefore, comprises providing a fluid source and a fluid-flow-producing means, a fluid conduit in fluid communication with the source, and a control device engaging and cooperating with the fluid conduit. The preferred method comprises providing the control device with a plurality of selector units, wherein each selector unit is moveable to partially flatten the fluid conduit to restrict flow to an extent that corresponds to a selected flow. The method may include de-selecting that selector unit, and selecting another, so as to adjust flow rate to various of the predetermined flows.

While the preferred embodiments are adapted for use with IV tubing for intravenous delivery of medicines, hydration fluids, blood, or other materials to a person or animal, other processes may benefit from the invention. For example, the inventor foresees that the invention could be used in many processes in which contamination of the fluid is undesirable, and/or contamination of the environment by the fluid is undesirable. Also, the flow control system may be beneficial in low flow rate processes, wherein expensive pump and control systems are not feasible. For example, the flow control system may be beneficial for many pilot plant and laboratory test stands that utilize flexible tubing, such as "Tygon™" tubing, for processes with flow-rates in the cc/min or cc/hour range.

Although this invention has been described above with reference to particular means, materials and embodiments, it is to be understood that the invention is not limited to these disclosed particulars, but extends instead to all equivalents within the scope of the following claims.

I claim:
1. A flow control system comprising:
   a fluid conduit tube having a flexible wall surrounding and defining an interior axial fluid passage; and
   a control device comprising a housing surrounding a portion of the tube and a plurality of selector units moveable in said housing away from the tube to an outward position and moveable in said housing to an inward position against and pressing on the tube so that the selector unit compresses the tube into reduced-cross-section shape to reduce flow through the axial fluid passage of the tube;

wherein each of said selector units in their fully inward positions compress the tube different amounts to reduce flow corresponding different amounts.

2. The flow control system as in claim 1, wherein said selector units are positioned in series along the tube, and each selector unit contacts a different portion of the tube.

3. The flow control system as in claim 1, wherein said selector units each have a bottom surface with a channel that receives the tube when the selector is in the inward position.

4. The flow control system as in claim 1, wherein the tube is an intravenous tube for delivering fluids to a patient.

5. The flow control system as in claim 1, wherein the control device has only three selector units, and each selector unit is differently shaped to cause different amounts of compression of the fluid conduit.

6. The control system as in claim 1, wherein the control device has only three selector units, and said three selector units are removable and interchangeable.

7. The control system as in claim 1, wherein each selector unit is moveable t said position by being depressed, and only one of said selector units is depressable at one time.

8. The control system as in claim 1, wherein each selector unit is moveable to said position by being depressed, and depressing one of said selector units causes any previously-depressed selector unit to release to an un-depressed position in which the fluid conduit is not flattened.

9. An intravenous fluid flow-rate control system comprising a single length of fluid conduit and a control device, the control device comprising a housing attached to the fluid conduit and a plurality of selector units moveably received in the housing, wherein each selector unit comprises a compression surface moveable to a fully inward position wherein the compression surface partially flattens the fluid conduit wherein the compression surface comprises two arms and a channel between the two arms, wherein, when the compression surface is moved to said fully inward position partially flattening the fluid conduit, the channel receives the fluid conduit and the two arms compress the fluid.

10. The control system as in claim 9, wherein the control device has only three selector units, and the compression surface of each of the three selector units is differently shaped to cause different amounts of flattening of the fluid conduit.

11. The control system as in claim 9, wherein the control device has only three selector units, and said three selector units are removable and interchangeable.

12. The control system as in claim 9, wherein each selector unit is moveable to said position by being depressed, and only one of said selector units is depressable at one time.

13. The control system as in claim 9, wherein each selector unit is moveable to said position by being depressed, and depressing one of said selector units causes any previously-depressed selector unit to release to an un-depressed position in which the fluid conduit is not flattened.

14. The control system as in claim 9, wherein the length of fluid conduit is intravenous tubing.

* * * * *